US006405066B1

United States Patent
Essenpreis et al.

(10) Patent No.: US 6,405,066 B1
(45) Date of Patent: Jun. 11, 2002

(54) IMPLANTABLE ANALYTE SENSOR

(75) Inventors: Matthias Essenpreis, Fremont, CA (US); Tejal A. Desai, Chicago, IL (US); Mauro Ferrari, Dublin; Derek J. Hansford, Columbus, both of OH (US)

(73) Assignees: The Regents of the University of California, Oakland, CA (US); Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/528,277

(22) Filed: Mar. 17, 2000

(51) Int. Cl.[7] .............................. A61B 5/05; A61B 5/04; G01N 27/26
(52) U.S. Cl. ..................... 600/347; 600/345; 600/377; 204/403; 204/415
(58) Field of Search ................................ 600/309, 316, 600/319, 345, 347, 365, 372, 373, 377; 204/403, 400, 415, 411, 412, 401

(56) References Cited

U.S. PATENT DOCUMENTS

| | | | | |
|---|---|---|---|---|
| 4,592,824 A | * | 6/1986 | Smith et al. | 204/416 |
| 4,832,797 A | * | 5/1989 | Vadgama et al. | 205/777 |
| 4,894,339 A | * | 1/1990 | Hanazato et al. | 435/182 |
| 4,971,901 A | * | 11/1990 | Hayashi et al. | 435/176 |
| 5,322,063 A | | 6/1994 | Allen et al. | 128/635 |
| 5,337,747 A | | 8/1994 | Neftel | 128/635 |
| 5,387,327 A | | 2/1995 | Khan | 204/403 |
| 5,411,647 A | | 5/1995 | Johnson et al. | 204/153.1 |
| 5,431,160 A | * | 7/1995 | Wilkins | 600/347 |
| 5,476,776 A | | 12/1995 | Wilkins | 435/176 |
| 5,660,163 A | | 8/1997 | Schulman et al. | 126/635 |
| 5,711,861 A | * | 1/1998 | Ward et al. | 600/347 |
| 5,711,868 A | * | 1/1998 | Maley et al. | 205/782.5 |
| 5,753,014 A | | 5/1998 | Van Rijn | 96/12 |
| 5,773,270 A | | 6/1998 | D'Orazio et al. | 435/177 |
| 5,837,454 A | | 11/1998 | Cozzette et al. | 435/6 |
| 5,874,047 A | | 2/1999 | Schöning et al. | 422/82.02 |
| 5,985,328 A | | 11/1999 | Chu et al. | 424/489 |
| 6,119,028 A | | 9/2000 | Schulman et al. | 600/345 |
| 6,201,980 B1 | * | 3/2001 | Darrow et al. | 600/347 |

FOREIGN PATENT DOCUMENTS

| | | | |
|---|---|---|---|
| EP | 0 284 518 A2 | 9/1988 | G01N/27/46 |
| WO | WO 91/15993 | 10/1991 | A61B/5/00 |
| WO | WO 94/20602 | 9/1994 | C12M/1/40 |
| WO | WO 96/06947 | 3/1996 | C12Q/1/54 |
| WO | WO 97/19344 | 5/1997 | G01N/27/26 |
| WO | WO 98/38906 | 9/1998 | A61B/5/00 |

OTHER PUBLICATIONS

Uwe Schanakenberg, Thomas Lisec, Raier Hintsche, Ingrid Kuna, Albrecht Uhlig, Bernd Wagner, "Novel potentiometric silicon sensor for medical devices," *Elsevier Science S.A.*, Sensors and Actuators B 34 (1996) 476–480.

Hansford, Derek James, "Microfabrication Materials for Biomedical Microdevices," Dissertation submitted to the University of California, Berkeley, Spring 1999, p. 10–14, 54, 56–58, 63, 68, 94, 95, 107, 108.

* cited by examiner

*Primary Examiner*—Kevin Shaver
*Assistant Examiner*—Navin Natnithithadha
(74) *Attorney, Agent, or Firm*—Brinks Hofer Gilson & Lione

(57) ABSTRACT

An implantable analyte sensor includes a substrate, electrodes on the substrate, and a membrane on the electrodes. The membrane can comprise elemental silicon and has a glucose diffusion test result of at least 1 mg/dl in 330 min., and an albumin diffusion test result of at most 0.1 g/dl in 420 min.

35 Claims, 3 Drawing Sheets

IMPLANTABLE ANALYTE SENSOR

BACKGROUND

The present invention relates to implantable analyte sensors.

Several implantable glucose sensors have been developed. Examples include those described in U.S. Pat. Nos. 5,387,327; 5,411,647; and 5,476,776; as well as those described in PCT International Publication numbers WO 91/15993; WO 94/20602; WO 96/06947; and WO 97/19344. The implantable glucose sensors usually include a polymer substrate, with metal electrodes printed on the surface of the substrate. A biocompatible membrane covers the electrodes, allowing glucose to reach the electrodes, while excluding other molecules, such as proteins. Electrochemistry, often with the aid of enzymes at the electrodes, is used to determine the quantity of glucose present. The glucose sensor is implanted into a patient, and the electrodes may be attached via wires that pass out of the patient's body to external circuitry that controls the electrodes, measures and reports the glucose concentration. Alternatively, all or part of this external circuitry may be miniaturized and included in the implantable glucose sensor. A transmitter, such as that described in WO 97/19344, may even be included in the implantable glucose sensor, completely eliminating the need for leads that pass out of the patient.

A problem associated with an amperometric glucose sensor is unstable signals. This may result from degradation of the enzyme from interaction with protein, leakage of the enzyme, and/or fouling of the electrode. The usual way to overcome this is to use the above described biocompatible membrane, or a coating. However, several problems are also associated with these membranes. For example, Nation-based biosensor membranes exhibit cracking, flaking, protein adhesion, and calcium deposits. Mineralization of polymer-based membranes occurs in the biological environment, resulting in cracking and changes in permeability. The tortuous porosity associated with polymer membranes has also been shown to be important in membrane stability and mineralization in vivo. Biological components, which enter pores or voids in the material, cause metabolic shadows, which are loci for ion and calcium accumulation. This situation, coupled with the fact that mineral deposits have been known to propagate surface fractures in polymeric membranes, presents a potentially serious problem for implantable glucose sensors.

In polymer membranes the pore size distribution usually follows some kind of probability distribution (e.g. gaussian), which leaves a finite probability for large proteins to eventually transfer through the membrane. Drift may be caused by this leakage or inadequate diffusion properties, and events at the body-sensor interface such as biofouling and protein adsorption, encapsulation with fibrotic tissue, and degradation of the device material over time.

Currently, membranes with nominal pore sizes as small as 20 nm are available. Even so, the filtration at these dimensions is far from absolute. The most common filters are polymeric membranes formed from a solvent-casting process, which result in a pore size distribution with variations as large as 30%. The use of ion-track etching to form membranes (e.g. MILLPORE ISOPORE) produces a much tighter pore size distribution (±10%). However, these membranes have low porosities (<$10^9$ pores/cm$^2$), limited pore sizes, and the pores are randomly distributed across the surface. Porous alumina (e.g. WHATMAN) has also been used to achieve uniform pores. Although the aluminas typically have higher pore densities (>$10^{10}$/cm$^2$), only certain pore sizes (typically greater than 20 nanometers) can be achieved and the pore configurations and arrangements are difficult to control.

BRIEF SUMMARY

In one aspect, the present invention is an implantable analyte sensor, comprising a substrate, electrodes on the substrate, and a membrane on the electrodes. The membrane has a glucose diffusion test result of at least 1 mg/dl in 330 min., and an albumin diffusion test result of at most 0.1 g/dl in 420 min. and can comprise elemental silicon.

In another aspect, the present invention relates to a method of making an implantable analyte sensor, comprising covering electrodes with a membrane. The electrodes are on a substrate, and the membrane has a glucose diffusion test result of at least 1 mg/dl in 330 min., and an albumin diffusion test result of at most 0.1 g/dl in 420 min. The membrane can comprise elemental silicon.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 10:
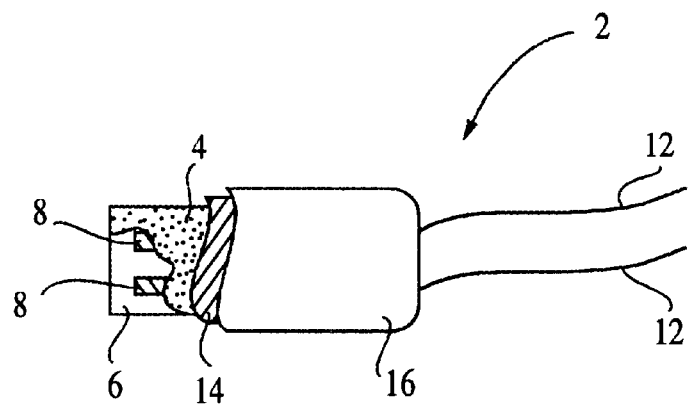
FIG. 10 shows a cut-away view of an implantable analyte sensor.

FIG. 10 shows a cut away view of an embodiment of the present invention. In the figure, an implantable analyte sensor 2 includes a substrate 6 on which are electrodes 8 and 8. The electrodes are covered with a membrane 4. Leads 12 and 12 allow for electrically connecting the implantable analyte sensor to external circuitry (not shown). The implantable analyte sensor also includes an external coating 16 and an internal coating 14.

Figure 11:
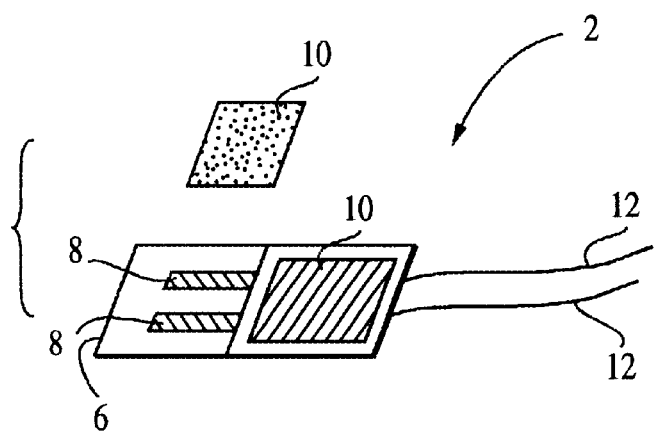
FIG. 11 shows an exploded view of an implantable analyte sensor.

FIG. 11 shows an exploded view of an embodiment of the present invention. The internal and external coatings are not included in the figure for clarity. As shown in the figure, the implantable analyte sensor 2 includes the electrodes 8 and 8 on the substrate 6 surface, which are electrically connected with microelectronic circuitry 10. The microelectronic circuitry is electrically connected to leads 12 and 12, which allow for electrically connecting the implantable analyte sensor to external circuitry (not shown). The electrodes are covered with the membrane 4.

Figure 12:
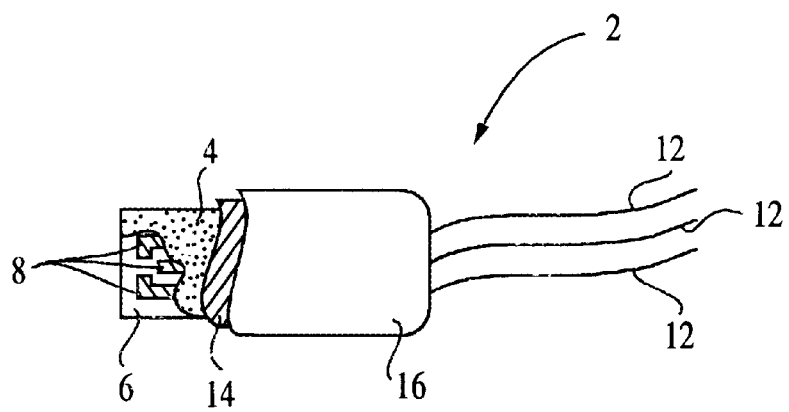
FIG. 12 shows a cut-away view of an implatable analyte sensor.

FIG. 12 shows a cut away view of an embodiment of the present invention similar to that shown in FIG. 10, except for the presence of a third electrode 8 and a third lead 12. Although so illustrated, the number of electrodes may be different from the number of leads.

The membrane is composed of a hard material that has been micromachined. Preferably, the membrane comprises elemental silicon, but other hard, biocompatable materials that can be micromachined are possible, such as metals (for example titanium), ceramics (for example, silica or silicon nitride), and polymers (such as polytetrafluoroethylene, polymethylmethacrylate, polystyrenes and silicones). Micromachining is a process that includes photolithography, such as that used in the semiconductor industry, to remove material from, or add material too, a substrate. These techniques are well known, and are described, in Encyclopedia of Chemical Technology, Kirk-Othmer, Volume 14, pp. 677–709 (1995): Semiconductor Device Fundamentals, Robert F. Pierret, Addison-Wesley, 1996; and Microchip Fabrication 3rd. edition, Peter Van Zant, McGraw-Hill, 1997. A detailed fabrication method for a membrane comprising elemental silicon is described in the dissertation of Derek James Hansford, submitted in partial satisfaction of the requirements for the degree of Doctor of Philosophy in Engineering-Materials Science and Mineral Engineering in the Graduate Division of the University of California, Berkeley, submitted in the spring of 1999.

A special property of the membrane is a defined pore size, which has a small size distribution compared to the size distribution of standard membranes. Due to tight tolerances in the manufacturing process, the pore size can be controlled at precise diameters, for example 1 to 50 nm, or 5 to 20 nm, or even 5 to 15 nm (such as 12 nm, 18 nm or even 25 nm), with a variation of +/−0.01–20%, +/−0.1–10% or even +/−1–5%. Therefore molecules above this size can be excluded with high certainty, since the size distribution has the shape of a top hat, rather than a bell curve, and hence pore sizes above, for example 12 nm, 18 nm, 25 nm or 50 nm are not present. These membranes can exclude interfering molecules, such as proteins, which could otherwise cause major drift problems of the sensor, when the sensor is implanted in vivo. Signal drift is a change in the magnitude of the signal from a sensor which is unrelated to changes in analyte concentration. The amount of signal drift is based on the magnitude of the signal prior to the drifting. Preferably, the implantable analyte sensors of the present invention exhibit a signal drift of less than 20% per day in vivo, more preferably less than 10% per day in vivo, most preferably less than 5% per day in vivo.

Membranes for use in the present invention may be characterized by a glucose diffusion test and an albumin diffusion test. These tests are described below. Preferably, the membrane has a glucose diffusion test result of at least 1 mg/dl in 330 min., more preferably at least 10 mg/dl in 330 min., even more preferably at least 30 mg/dl in 330 min., and most preferably at least 60 mg/dl in 330 min. Preferably, the membrane has an albumin diffusion test result of at most 0.1 g/dl in 420 min., more preferably at most 0.05 g/dl in 420 min., even more preferably at most 0.01 g/dl in 420 min., and most preferably at most 0.001 g/dl in 420 min.

The manufacturing process of the membranes may allow a simple and economical production of small, implantable analyte sensors. For example, the membranes can be first manufactured, and then on a substrate, the electrodes for the sensor and the electrical connectors can be formed. Preferably, the substrate is silicon, but other materials are possible, such as ceramics, or polymers. If desired, electronic components, for example, amplifiers, filters, transmitters and/or signal preconditioning components, can easily be incorporated in this layer. In particular, if the substrate comprises elemental silicon, well known integrated circuit technology may be used to place all the circuitry in miniaturized form on a single chip.

There are two possible approaches to attach the substrate and the membrane, when a reagent is included in the sensor.

1. The substrate and the membrane are thermally bonded before the reagent is deposited on the electrodes. In this case, an opening, preferably in the membrane is provided (since this may be manufactured with a micromachining process, an opening is easily generated during one of the processing steps). In the case where multiple membranes are formed as a single piece, and or multiple substrates are formed as a single piece, after thermal bonding, a further etching step may be used to separate the individual membrane/substrate units. The reagent is deposited through the individual openings and the openings are sealed using, for example a polymer sealant. The individual sensors are then separated, incorporated into a flexible, inner coating, for example silicone rubber, and individually coated with an outer coating, such as a biocompatible layer.

2. The reagent is deposited on the electrodes before the membrane and substrate are attached. In this case, thermal bonding is not possible, since the enzyme in the reagent would be destroyed. The individual membranes and substrates are first separated and the individual sensors are assembled by bonding one membrane with one substrate using a suitable bonding agent, for example, cyanoacrylate. As a final step, the individual sensors are incorporated into a flexible, inner coating, for example silicone rubber, and individually coated with an outer coating, such as a biocompatible layer. The sensor can be inserted into the skin using a needle applicator. The control unit typically remains outside the body and can be connected to the sensor element through electrical wires (leads).

The electrodes are formed on the surface of the substrate. They may be formed by well known semiconductor processing techniques, from conductive materials, such as pure metals or alloys, or other materials which are metallic conductors. Examples include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or metallic compounds of these elements. Preferably, the electrodes include gold, platinum, palladium, iridium, or alloys of these metals, since such noble metals and their alloys are unreactive in biological systems. The electrodes may be any thickness, but preferably are 10 nm to 1 mm, more preferably, 20 nm to 100 µm, or even 25 nm to 1 µm.

At least two electrodes must be present. The number of electrodes may be 2–1000, or 3–200, or even 3–99. Individual electrode sets (2 or 3 electrodes) may be separated into individual chambers, each covered with the membrane. Furthermore, individual electrode sets (2 or 3 electrodes) may each have a different reagent, allowing for an implantable analyte sensor that can measure at least two, such as 3–100, or 4–20, different analytes.

The remaining individual part of the implantable analyte sensors are well known to those of ordinary skill in the art, and are described, for example, in U.S. Pat. Nos. 5,387,327; 5,411,647; and 5,476,776; as well as in PCT International Publication numbers WO 91/15993; WO 94/20602; WO 96/06947; and WO 97/19344.

Although illustrated with both leads and microelectronic circuitry, these components are optional. The microelectronic circuitry may include some or all of the electrical components normally external to the implantable analyte sensor, such as a microprocessor, an amplifier, or a power supply. If the microelectronic circuitry also includes a transmitter, or another device for sending information wirelessly, such as a laser which emits light through the skin, then there is no need to include the leads. Alternatively, the microelectronic circuitry may not be present, in which case the lead will directly electrically connect the electrodes with external electrical components.

Optionally, one or more internal coatings may be present. The internal coating may function to regulate diffusion. Examples of internal coatings include cellulose acetate, polyurethane, polyallylamines (PAL), polyaziridine (PAZ), and silicon-containing polymers. Some specific examples are described in PCT Publications WO 98/17995, WO 98/13685 and WO 96/06947, and in U.S. Pat. Nos. 4,650,547 and 5,165,407.

Optionally, one or more external coatings may be present. The implantable analyte sensors of the present invention are intended to be used in vivo, preferably subcutaneously in mammals, such as humans, dogs or mice. The external coatings function to improve the biocompatibility of the implantable analyte sensor. Examples of external coatings include nafion, polyurethanes, polytetrafluoroethylenes (PTFE), poly (ethylene oxide) (PEO), and 2-methacryloyloxyethyl phosphorylcholine-co-n-butyl methacrylate (MPC) membranes. Some specific examples are described in PCT Publication WO 96/06947, and in "Medical Progress through Technology", Nishida et al. 21: 91–103 (1995)).

The electrodes may be coated with a reagent. The reagent is optional, and may be used to provide electrochemical probes for specific analytes. The reagent may be as simple as a single enzyme, such as glucose oxidase or glucose hydrogenase for the detection of glucose. The enzyme may be immobilized or "wired" as described in PCT Publication WO 96/06947. The reagents may optionally also include a mediator, to enhance sensitivity of the sensor. The starting reagents are the reactants or components of the reagent, and are often compounded together in liquid form before application to the electrodes. The liquid may then evaporate, leaving the reagent in solid form. The choice of specific reagent depends on the specific analyte or analytes to be measured, and are well known to those of ordinary skill in the art. For example, a reagent for measurement of glucose can contain 62.2 mg polyethylene oxide (mean molecular weight of 100–900 kilodaltons), 3.3 mg NATROSOL 250 M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase, forming a solution of quinoprotein glucose dehydrogenase. This reagent is described in WO 99/30152, pages 7–10, hereby incorporated by referece.

Other non-limiting examples of enzymes and optional mediators that may be used in measuring particular analytes in the present invention are listed below in Table 1.

TABLE 1

| Analyte | Enzymes | Mediator (Oxidized Form) | Additional Mediator |
| --- | --- | --- | --- |
| Glucose | Glucose Dehydrogenase and Diaphorase | Ferricyanide | |

TABLE 1-continued

| Analyte | Enzymes | Mediator (Oxidized Form) | Additional Mediator |
| --- | --- | --- | --- |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is appreciated that a variety of electrochemical assays may be conducted in accordance with this disclosure.

Formation of Membrane

The following describes how to make a membrane for use in the present invention, based on the description from the dissertation of Derek James Hansford, submitted in partial satisfaction of the requirements for the degree of Doctor of Philosophy in Engineering-Materials Science and Mineral Engineering in the Graduate Division of the University of California, Berkeley, submitted in the spring of 1999.

Other membranes, made from other material, may also be used. This specific method relies upon a buried nitride etch stop layer.

The buried nitride etch stop layer acts as an etchant stop during the formation of nanometer scale pores. The buried nitride etch stop layer facilitates three-dimensional control of the pore structure, and facilitates the formation of pores less than 50 nanometers in diameter. Moreover, these pores can be uniformly formed across the entire wafer.

Preferably, the first step in the fabrication protocol is to etch a support ridge structure into a substrate. The ridges provide mechanical rigidity to the subsequently formed membrane structure.

Figure 1:
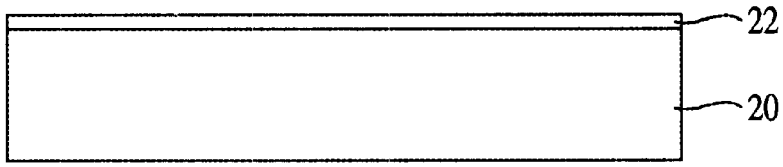
FIGS. 1–9 illustrate the process of making a membrane for use in an embodiment of the present invention.

A low stress silicon nitride (LSN or nitride), which operates as an etch stop layer, is then deposited on the substrate using low pressure chemical vapor depositions (LPCVD). In one embodiment, 0.4 µm of nitride was used. The resultant structure is shown in FIG. 1. FIG. 1 illustrates a substrate 20 with a nitride etch stop layer 22 formed thereon.

Figure 2:
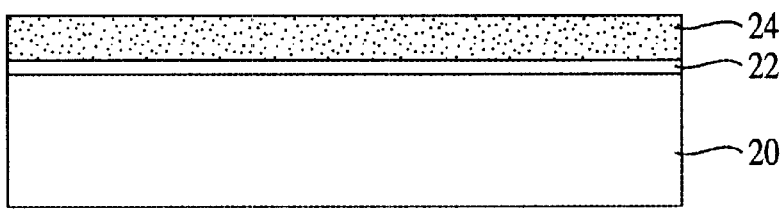

The base structural layer (base layer) of the membrane is deposited on top of the stop layer 22. Since the etch stop layer 22 is thin, the structural layer is deposited down into the support ridges formed in the substrate 20. In one embodiment, 5 µm of polysilicon is used as the base layer. FIG. 2 illustrates the base layer 24 positioned on the etch stop layer 22. Low stress silicon nitride may also be used as the base layer, in which case it operates as it own etch stop layer.

Figure 3:
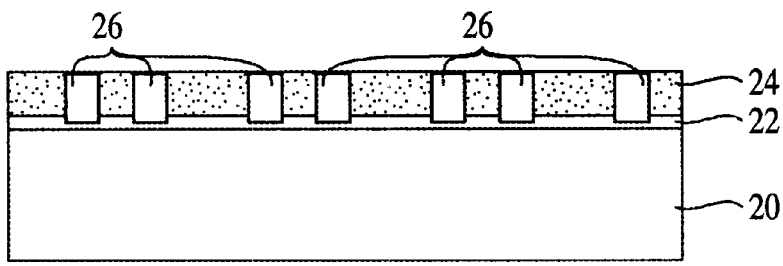

The next processing step is to etch holes in the base layer 24 to define the shape of the pores. Masks, such as those used in traditional semiconductor processing, may be used to define the pores. For example, the holes may be etched through the polysilicon by chlorine plasma, with a thermally grown oxide layer used as a mask. In this step, it is important to make sure the etching goes completely through the base layer 24, so a 10–15% overetch is preferably used. It is useful to note that the buried nitride etch stop 22 acts as an etch stop for the plasma etching of a silicon base layer 24. Otherwise, if the plasma punched through the nitride, tighter control of the etch step would have to be exercised to prevent the complete removal of the nitride under the plug layer (to prevent removal in the final KOH etch). FIG. 3 illustrates the result of this processing. In particular, the figure illustrates holes 26 formed in the base layer 24, but terminating in the nitride etch stop layer 22.

Figure 4:
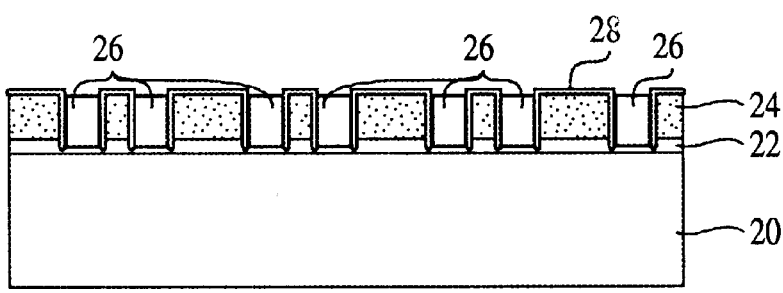

Pore sacrificial oxide is subsequently grown on the base layer 24. FIG. 4 illustrates a sacrificial oxide 28 positioned on the base layer 24.

The sacrificial oxide thickness determines the pore size in the final membrane, so control of this step is critical to reproducible membranes. This is accomplished by the thermal oxidation of the base layer 24(e.g., a growth temperature of between 850–950° C. for approximately one hour with a ten minute anneal). Naturally, many techniques may be used to form a controlled thickness sacrificial layer. For example, a thermally evaporated tungsten film may be used as a sacrificial layer for polymer membranes and selectively removed with hydrogen peroxide. The basic requirement of the sacrificial layer is the ability to control the thickness with high precision across the entire wafer. Thermal oxidation of both polysilicon and nitride allows the control of the sacrificial layer thickness of less than 5% across the entire wafer. Limitations on this control arise from local inhomogeneities in the base layer, such as the initial thickness of the native oxide (especially for polysilicon) the grain size or the density, and the impurity concentrations.

Figure 5:
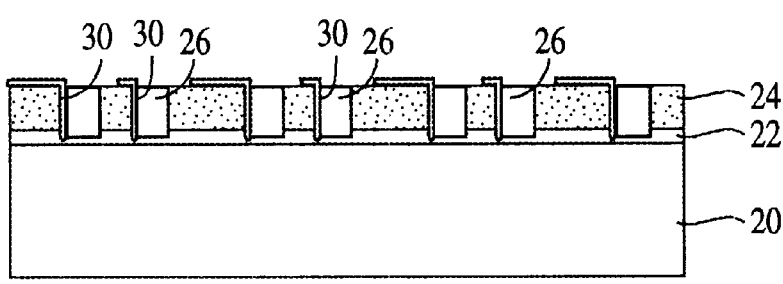

To mechanically connect the base layer 24 with the plug layer (necessary to maintain the pore spacing between layers), anchor points were defined in the sacrificial oxide layer 26. In the present design, this is accomplished by using the same mask shifted from the pore holes by 1 µm diagonally. This produced anchors in one or two corners of each pore hole, which provides the desired mechanical connection between the structural layers while opening the pore area as much as possible. FIG. 5 illustrates anchors 30 formed via this process.

Figure 6:
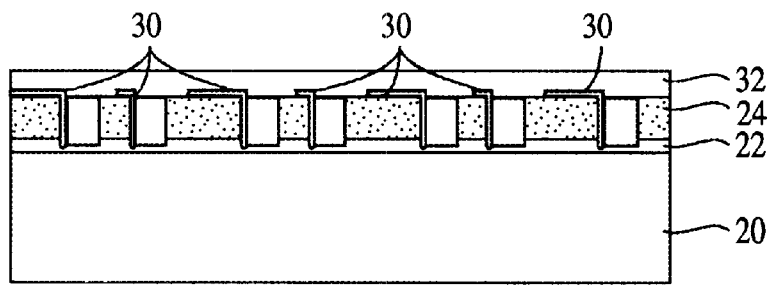

A plug structural layer is subsequently deposited to fill in the holes 26. This step has been implemented by depositing 1.5 µm of polysilicon. The resultant plug layer 32 is shown in FIG. 6.

Figure 7:
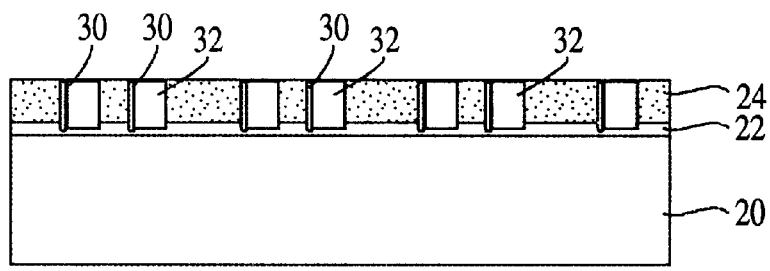

To open the pores at the surface, the plug layer 32 is planarized down to the base layer, leaving the final structure with the plug layer only in the pore hole openings, as shown in FIG. 7.

The method of planarization depends on the material used as the plug material. For the hard micro-fabrication materials (polysilicon and nitride), chemical mechanical polishing was used for planarization. The other materials studied were roughly planarized using a plasma etch, with a quick wet chemical smoothing. This technique has the advantage that, assuming it is not etched by the plasma used, the base layer is not affected, but has the disadvantage of the need for controlled etch timing to avoid completely etching the plugs themselves.

At this point, the membrane is ready for release, so a protective layer 34 is deposited on the wafer (completely covering both sides of the wafer). The requirements of the protective layer 34 are that it be impervious to the silicon etch (KOH for these studies) and that it be removed without removing the plug 32 or base 24 structural layers. For polysilicon and nitride structural layers, a thin nitride layer is used as the protective layer (nitride is not etched at all by KOH and dissolves slowly in HF). For polymeric structural materials, silicon is used as a protective layer, due to the processing temperature necessary for nitride deposition (835° C.).

Figure 8:
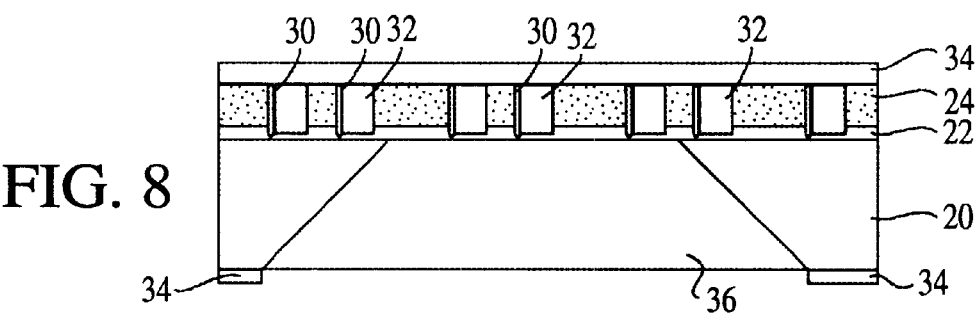

The backside etch windows were etched in the protective layer, exposing the silicon in desired areas, and then the entire structure was placed in an 80° C. KOH bath until the silicon wafer substrate 20 is etched up to the membrane base layer 24 (as evidenced by the smooth buried etch stop layer). FIG. 8 illustrates the resultant aperture 36 formed in the substrate 20.

Figure 9:
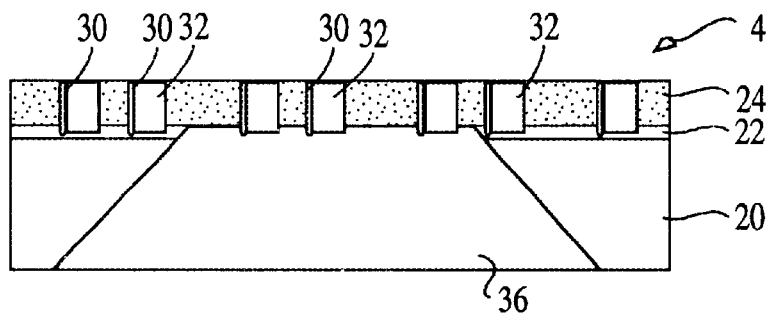

At this point, the buried nitride layer 22, the sacrificial oxide layer 34, and plug layer 32 are removed by etching in HF or $SF_6$/oxygen plasma. The resultant membrane 4 with nanometer scale pores is shown in FIG. 9.

Characterization of Membranes

The purpose of the membranes is to allow the analyte of interest (such as glucose) to diffuse through the membrane, while excluding large molecules (such as proteins). Therefore, two important characteristics of the membranes are glucose diffusion and albumin diffusion. All tests are carried out at room temperature (25° C.).

The following is a glucose diffusion test:

Diffusion of glucose is measured using a mini diffusion chamber constructed around the membranes. The diffusion chamber, fabricated out of acrylic, consists of two compartments A and B with fixed volumes of 2 ml, separated by the desired membrane, sealed with o-rings, and screwed together.

Glucose is measured on either side of the membrane using the diffusion chamber by means of a quantitative enzymatic assay (TRINDER™, SIGMA) and colorometric reading via a spectrophotometer. Starting glucose concentrations for all tests were 6,666 mg/dl and 0.0 mg/dl in chambers A and B, respectively. Samples of 0.1 ml are taken from the diffusion chamber and 10 µl of that are added to 3 ml of glucose reagent in a cuvette, and mixed gently by inversion. Each tube is incubated for 18 minutes at room temperature and then readings are taken at a wavelength of 505 nm. The reagent is linear up to 750 mg/dl. The diffusion chamber itself is attached to a motor for stirring in order to minimize boundary layer effects (diffusion resistance at the liquid/ membrane interface). In order to ensure wetting of the pores, the receptor cell is first filled with phosphate buffer saline (PBS) for fifteen minutes before the filling of the donor cell. The donor cell is filled with solutions of glucose in PBS in varying concentrations.

The following is an albumin diffusion test:

Albumin is also measured on either side of the membrane using the same diffusion chamber as in the glucose diffusion test. Albumin diffusion and/or exclusion is first measured and quantified using Albumin BCP (bromocresol purple, SIGMA). Starting albumin concentrations for all tests are 4 g/dl and 0.0 mg/dl in chambers A and B, respectively. A sample of 0.1 ml is taken at time zero and at the end of the diffusion period (time=330 minutes). An aliquot of 300 μl is then added to 3 ml of the reagent and absorbence is read at 600 nm. Reagent plus deionized water is used as the blank. The BCP assay is linear up to 6 g/dl but is not accurate below 1 g/dl. For the small concentration of albumin that might be present in chamber A, the presence of any protein in chamber B is measured using the Bradford Method (MICRO PROTEIN KIT, SIGMA). This method quantitates the binding of Coomassie brilliant blue to an unknown protein and compares this binding to that of different amounts of a standard protein. Albumin is used as a standard protein. This method quantifies 1 to 100 micrograms protein using a standard curve, with sensitivity down to 10 mg/dl or 0.1 g/dl protein. The absorbance is measured at 595 nm.

Analysis of Membranes

Diffusion of glucose was measured for three types of membranes: silicon micromachined membranes (average pore size=0.0245 microns), WHATMAN ANODISC membranes (average pore size=0.02 microns), and MF-MILLIPORE mixed cellulose acetate and nitrate membrane (average pore size=0.025 microns).

The results from the albumin test are shown in the table below.

| time | WHATMAN albumin conc. (g/dL) | MILLIPORE albumin conc. (g/dL) | silicon (micromachined) albumin conc. (g/dL) |
|---|---|---|---|
| 0 | 0 | 0 | 0 |
| 420 Min. | 0.25±0.05 | 0.2±0.01 | 0±0.001 |

The presence of albumin does not seem to impede passage of glucose through the membranes, nor slow down glucose transport. No detectable amounts of albumin diffuse through the micromachined membrane. The same membrane, however, shows glucose diffusion. The micromachined membranes are able to achieve complete exclusion of albumin (to within the limits of detection), while allowing glucose diffusion. Comparing diffusion rates with that of commercially available membranes, the micromachined membranes have glucose diffusion properties comparable to MILLIPORE and alumina WHATMAN membranes with similar pore sizes.

The passage of albumin through the micromachined membrane is measured by looking at the change of albumin concentration in chamber A and chamber B over time. Using the BCP assay, there are no detectable traces of albumin in chamber B. However, the amount of albumin in chamber B may have been below the limits of detectability of this assay system. Therefore, the Bradford Method was also employed. Using this microassay, again no detectable amounts of albumin were found in chamber B for the micromachined membrane, but small amounts of protein were found in chamber B using both the MILLIPORE and WHATMAN membranes. The amounts of albumin detected after 420 minutes in chamber B were approximately 0.25 g/dl and 0.20 g/dl albumin for the MILLIPORE and WHATMAN membranes, respectively.

Glucose does diffuse through micromachined membranes at a rate comparable to commercially available membranes. At the same time, albumin is excluded from passage. In mixed solutions of glucose and albumin, only glucose diffuses through the micromachined membranes.

What is claimed is:

1. An implantable analyte sensor, comprising:
    (a) a substrate,
    (b) electrodes on said substrate, and
    (c) a membrane on said electrodes,
    wherein said membrane comprises elemental silicon and has a glucose diffusion test result of at least 1 mg/dl in 330 min., and an albumin diffusion test result of at most 0.1 g/dl in 420 min.

2. The implantable analyte sensor of claim 1, further comprising:
    (d) microelectronic circuitry electrically connected to said electrodes.

3. The implantable analyte sensor of claim 1, further comprising:
    (e) leads electrically connected to said electrodes.

4. The implantable analyte sensor of claim 2, further comprising:
    (e) leads electrically connected to said electrodes,
    wherein said leads are electrically connected to said electrodes via said microelectronic circuitry.

5. The implantable analyte sensor of claim 2, wherein said microelectronic circuitry comprises a transmitter and a power supply.

6. The implantable analyte sensor of claim 1, further comprising:
    (f) a coating surrounding said substrate and said membrane.

7. The implantable analyte sensor of claim 6, wherein said coating comprises an internal coating and an external coating.

8. The implantable analyte sensor of claim 1, wherein said substrate comprises elemental silicon.

9. The implantable analyte sensor of claim 1, wherein said membrane is prepared by micromachining.

10. The implantable analyte sensor of claim 1, wherein said glucose diffusion test result is at least 60 mg/dl in 330 min., and said albumin diffusion test result is at most 0.001 g/dl in 420 min.

11. The implantable analyte sensor of claim 1, wherein the implantable analyte sensor is a glucose sensor.

12. An implantable analyte sensor, comprising:
    (a) a substrate,
    (b) electrodes on said substrate, and
    (c) a membrane on said electrodes,
    wherein said membrane has a glucose diffusion test result of at least 1 mg/dl in 330 min., and an albumin diffusion test result of at most 0.1 g/dl in 420 min.

13. The implantable analyte sensor of claim 12, wherein said glucose diffusion test result is at least 60 mg/dl in 330 min., and said albumin diffusion test result is at most 0.001 g/dl in 420 min.

14. The implantable analyte sensor of claim 12, further comprising:
    (d) microelectronic circuitry electrically connected to said electrodes.

15. The implantable analyte sensor of claim 12, further comprising:

(e) leads electrically connected to said electrodes.

16. The implantable analyte sensor of claim 14, further comprising:

(e) leads electrically connected to said electrodes, wherein said leads are electrically connected to said electrodes via said microelectronic circuitry.

17. The implantable analyte sensor of claim 14, wherein said microelectronic circuitry comprises a transmitter and a power supply.

18. The implantable analyte sensor of claim 12, further comprising:

(f) a coating surrounding said substrate and said membrane.

19. The implantable analyte sensor of claim 18, wherein said coating comprises an internal coating and an external coating.

20. The implantable analyte sensor of claim 12, wherein said substrate comprises elemental silicon.

21. The implantable analyte sensor of claim 12, wherein said membrane is prepared by micromachining.

22. The implantable analyte sensor of claim 12, wherein the implantable analyte sensor is a glucose sensor.

23. A method of making an implantable analyte sensor, comprising:

covering electrodes with a membrane;

wherein said electrodes are on a substrate and said membrane comprises elemental silicon and has a glucose diffusion test result of at least 1 mg/dl in 330 min., and an albumin diffusion test result of at most 0.1 g/dl in 420 min.

24. The method of claim 23, further comprising:

forming said membrane by micromachining elemental silicon.

25. The method of claim 23, further comprising:

surrounding said membrane and said substrate with a coating.

26. The method of claim 23, wherein said glucose diffusion test result is at least 60 mg/dl in 330 min., and said albumin diffusion test result is at most 0.001 g/dl in 420 min.

27. The method of claim 23, wherein the implantable analyte sensor is a glucose sensor.

28. A method of making an implantable analyte sensor, comprising:

covering electrodes with a membrane, wherein said electrodes are on a substrate, and said membrane has a glucose diffusion test result of at least 1 mg/dl in 330 min., and an albumin diffusion test result of at most 0.1 g/dl in 420 min.

29. The method of claim 28, further comprising:

forming said membrane by micromachining elemental silicon.

30. The method of claim 28, further comprising:

surrounding said membrane and said substrate with a coating.

31. The method of claim 28, wherein said glucose diffusion test result is at least 60 mg/dl in 330 min., and said albumin diffusion test result is at most 0.001 g/dl in 420 min.

32. The method of claim 28, wherein said membrane is prepared by micromachining.

33. The method of claim 28, wherein the implantable analyte sensor is a glucose sensor.

34. In an implantable analyte sensor including electrodes on a substrate and a membrane covering the electrodes, the improvement comprising the membrane having a glucose diffusion test result of at least 1 mg/dl in 330 min., and an albumin diffusion test result of at most 0.1 g/dl in 420 min.

35. An implantable analyte sensor, comprising:

(i) means for measuring an analyte electrochemically, and (ii) a membrane on said means, wherein said membrane has a glucose diffusion test result of at least 1 mg/dl in 330 min., and an albumin diffusion test result of at most 0.1 g/dl in 420 min.

* * * * *